United States Patent
Jewell, Jr. et al.

[11] Patent Number: 4,625,039
[45] Date of Patent: Nov. 25, 1986

[54] 4-TRISUBSTITUTED SILYL PROTECTED HYDROXY-6-OXO-TETRAHYDROPYRAN-2-YL-ALDEHYDE INTERMEDIATES

[75] Inventors: Charles F. Jewell, Jr., Budd Lake; James R. Wareing, Randolph, both of N.J.

[73] Assignee: Sandoz Pharm. Corp., E. Hanover, N.J.

[21] Appl. No.: 563,945

[22] Filed: Dec. 21, 1983

[51] Int. Cl.$^4$ ............................................. C07D 309/30
[52] U.S. Cl. ..................................... 549/214; 549/292; 548/494
[58] Field of Search ................. 549/214, 292; 548/494

[56] References Cited

U.S. PATENT DOCUMENTS 4,474,971 10/1984 Wareing .............................. 549/214

OTHER PUBLICATIONS

Katoitzky, "Advances in Heterocyclic Chemistry", vol. 2, p. 301, Academic Press, 1963.
House, "Modern Synthetic Reactions", 2nd ed., pp. 692–693.
Morrison, "Organic Chemistry", 3rd ed., pp. 218–219.

*Primary Examiner*—David M. Naff
*Assistant Examiner*—Robert Benson
*Attorney, Agent, or Firm*—Gerald D. Sharkin; Richard E. Vila; Frederick H. Weinfeldt

[57] ABSTRACT

6-trans-indol-2-yl-ethenyl)-4-hydroxy-tetrahydro-2H-pyran-2-ones of formula I are obtained by a multi-step reaction involving the procedure:

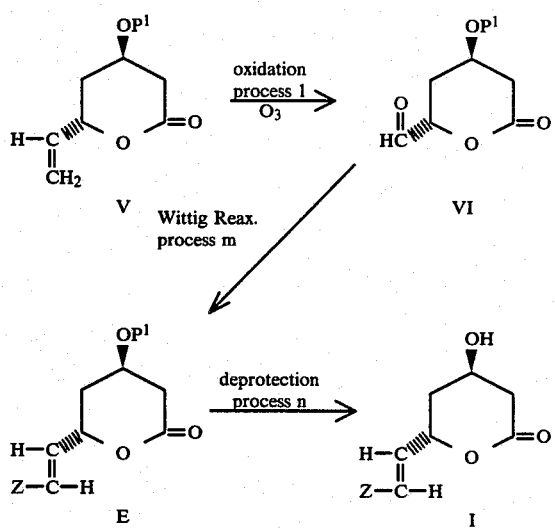

wherein $p^1$ is trisubstituted silyl protective group, and Z is a 2-indolyl radical which may be bear at the 4, 5, 6 and 7-positions up to two substituents such as alkyl, alkoxy, halo and $CF_3$, and at either one the 1 or 3-positions a substituted or unsubstituted phenyl; and at the other an assymetric alkyl, cycloalkyl or aralkyl radical. Compounds I, e.g. (E)-trans-6-[1'-methyl-3'-(4"-fluorophenyl)indol-2'-ylethenyl]3,4,5,6-tetrahydro-4-hydroxy-2H-pyran-2-one(4R,6S); are useful as antiatheroselerotic agents.

4 Claims, No Drawings

4-TRISUBSTITUTED SILYL PROTECTED HYDROXY-6-OXO-TETRAHYDROPYRAN-2-YL-ALDEHYDE INTERMEDIATES

This invention relates to a process for preparing organic compounds, and more specifically for preparing 6-substituted-4-hydroxy-tetrahydropyran-2-ones, as well as intermediates, per se in the process.

This invention provides a novel process for the preparation of 6-trans-olefinically-substituted tetrahydropyran-2-ones of the formula I:

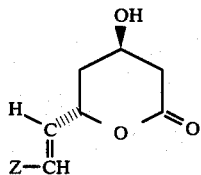

wherein Z is a radical of the formula:

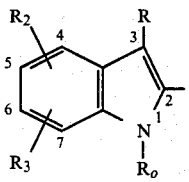

wherein
one of R and $R_o$ is

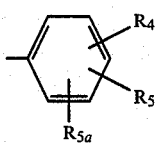

and the other is primary or secondary $C_{1-6}$alkyl not containing an asymmetric carbon atom, $C_{3-6}$cycloalkyl or phenyl $(CH_2)_m$—, wherein
$R_4$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R_5$ is hydrogen, $C_{1-3}$alkyl, $C_{1-3}$alkoxy, trifluoromethyl, fluoro, chloro, phenoxy or benzyloxy;
$R_{5a}$ is hydrogen, $C_{1-2}$alkyl, $C_{1-2}$alkoxy, fluoro or chloro; and
m is 1, 2 or 3; with the provisos that both $R_5$ and $R_{5a}$ must be hydrogen when $R_4$ is hydrogen, $R_{5a}$ must be hydrogen when $R_5$ is hydrogen, not more than one of $R_4$ and $R_5$ is trifluoromethyl, not more than one of $R_4$ and $R_5$ is phenoxy and not more than one of $R_4$ and $R_5$ is benzyloxy;
$R_2$ is hydrogen, $C_{1-3}$alkyl, n-butyl, i-butyl, t-butyl, $C_{3-6}$cycloalkyl, $C_{1-3}$alkoxy, n-butoxy, i-butoxy, trifluoromethyl, fluoro, chloro, phenoxy or benzyloxy;
$R_3$ is hydrogen, $C_{1-3}$alkyl, $C_{1-3}$alkoxy, trifluoromethyl, fluoro, chloro, phenoxy or benzyloxy; with the provisos that $R_3$ must be hydrogen when $R_2$ is hydrogen, not more than one of $R_2$ and $R_3$ is phenoxy, and not more than one of $R_2$ and $R_3$ is benzyloxy.

The terms "halogen" and "halo" as used in the definition of compounds I is intended to include fluoro and chloro.

Compounds I are disclosed in copending application Ser. No. 707,854 of F. G. Kathawala, filed Mar. 4, 1985, which is a continuation of application Ser. No. 548,850, filed Nov. 4, 1983, now abandoned, which is a continuation-in-part of application Ser. No. 443,668, filed Nov. 22, 1982, now abandoned, and are useful as anti-hypercholestermic agents as they are inhibitors of cholesterol biosynthesis in the manner of the known products compactin and mevinolin and are therefore useful in the treatment of atherosclerosis, as described in said application.

An embodiment of this invention is a multi-step process for the preparation of compounds I, which process may conveniently be represented by Reaction Scheme A, below, wherein Z is as defined above, and $P^1$ and $P^2$ are protective groups.

REACTION SCHEME A

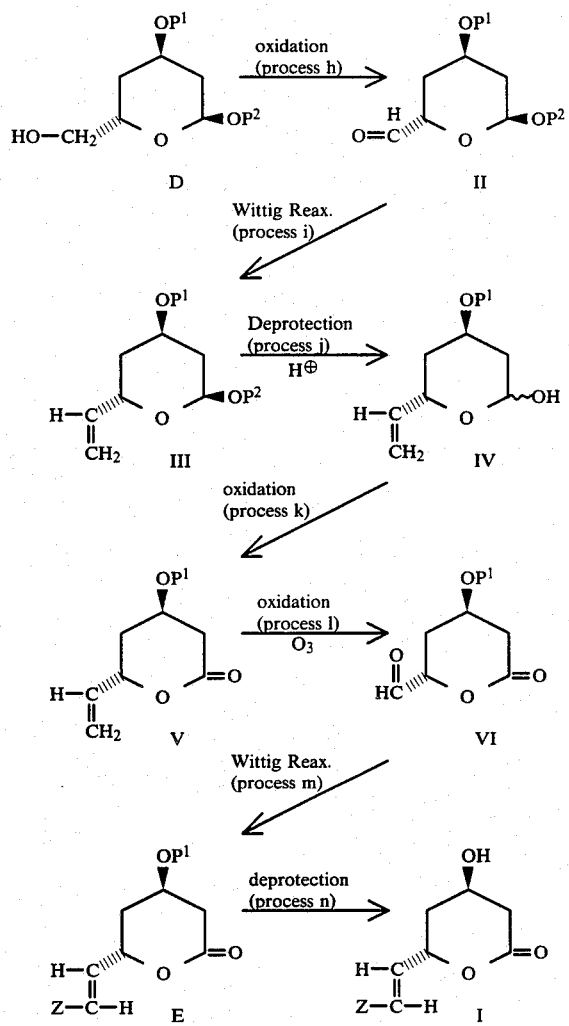

Compounds II depicted in Reaction Scheme A, above, are obtainable by a series of reaction steps shown in Reaction Scheme B, below, starting with a Compound A. Compounds A, in turn, are obtainable by a series of reaction steps shown in Reaction Scheme C, below, starting with the known compound W.

The preparation of Compounds II of this invention via Reaction Schemes B and C is disclosed in U.S. Pat. No. 4,474,971 (issued Oct. 2, 1984) identified therein as compounds V.

In reaction Schemes B and C, $P^1$ and $P^2$ are as defined above and $P^3$ is a protective group, Ac is acetyl, ipr is isopropyl and X is a leaving group e.g. iodo or bromo.

An advantage of this invention is that compounds I in the 4R,6S, enantiomer form may be prepared where starting materials have such form, e.g. compounds D; thus avoiding the difficulty of separating isomeric forms where such a form is desired.

REACTION SCHEME B

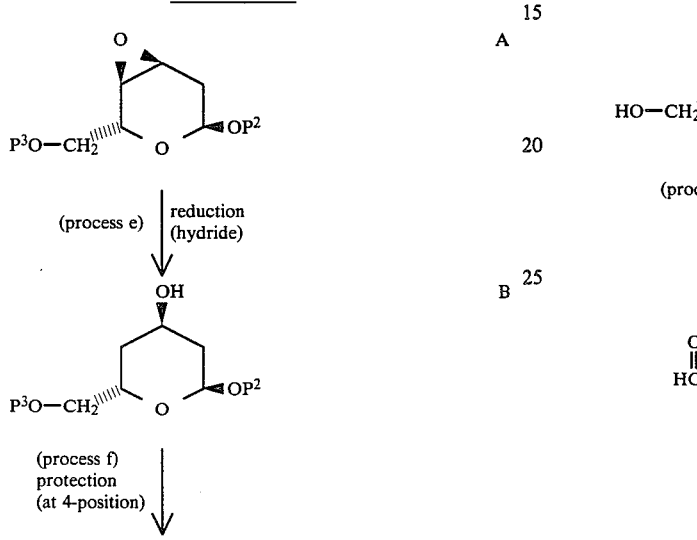

-continued
REACTION SCHEME B

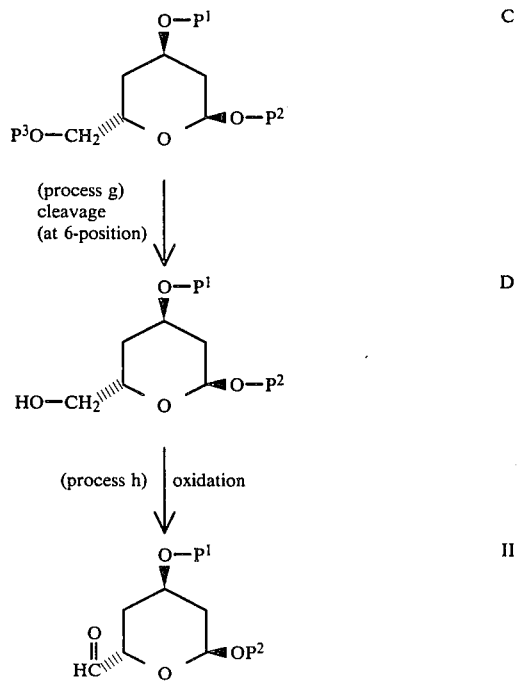

REACTION SCHEME C

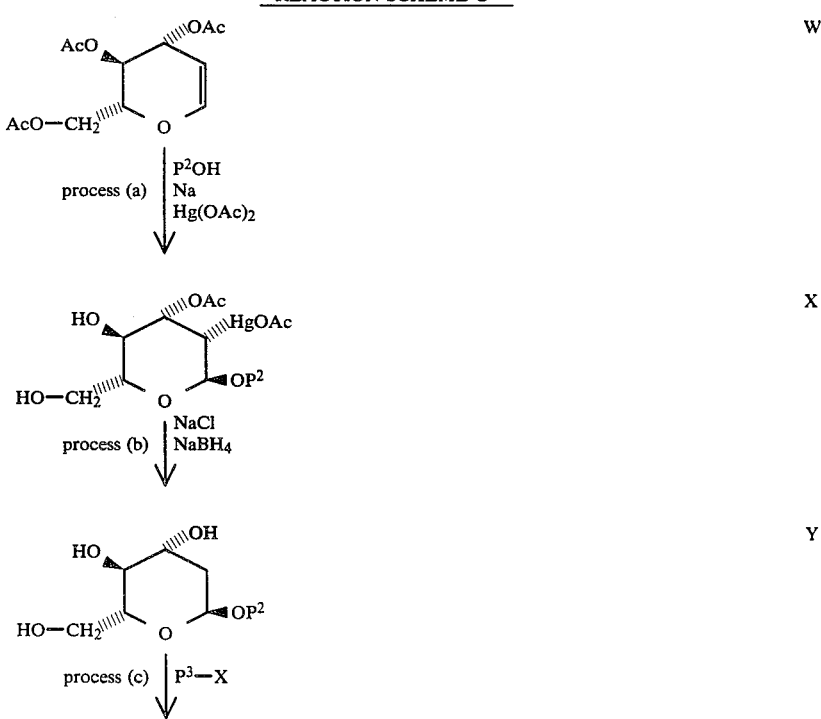

-continued
REACTION SCHEME C

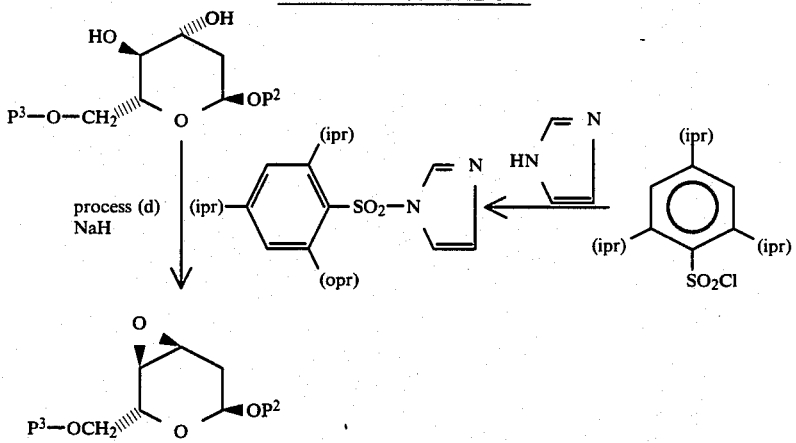

Alternatively, a protected-2α-hydroxy isomer of compounds II i.e. II' may be employed therefor, since the protecting group is removed at process (j) to obtain a 2α-form of a compound IV in which the geometric orientation of unprotected hydroxy group is not critical as it will subsequently by oxidized to a carbonyl-function in process (k). A compound II' is also obtainable as reported by Yang et al in Tetrahedron Letters 23, 4305 (1982), as structure No. 7.

Compounds II can also be obtained by oxidizing the 2α-hydroxymethyl substituent of a corresponding analog. Such hydroxymethyl-bearing analogs are obtainable by the process disclosed in copending application Ser. No. 367,280 (filed Apr. 12, 1982, now abandoned) as compounds L thereof. The oxidation (process (h')) may be carried out in the conventional manner for oxidizing a hydroxymethyl compound to its corresponding aldehyde, e.g. by use of pyridinium chlorochromate or the Swern procedure.

It will be noted in the Reaction Schemes, above, that the protecting groups $P^1$, $P^2$ and $P^3$ are introduced and removed (deprotected) at various stages in the overall process, i.e., no more than one type at a time. Hence, all three protecting groups $P^1$, $P^2$ and $P^3$ are preferably different, so that by choice of particular groups to be employed and selection of reaction conditions, deprotection at a desired position can be achieved, while retaining any other protecting groups as desired. Indeed, intermediates C are shown in Reaction Scheme B to bear 3 protecting groups.

Suitable protective groups $P^1$, include 1) tri-substituted silyl radicals have at least 2, and preferably 3 bulky radicals, i.e. radicals selected from the group consisting of a) tertiary alkyl ($C_4$ to $C_8$) groups especially t-butyl, and b) aryl, preferably phenyl which may be unsubstituted or substituted by up to 2 (preferably 0 or 1) of any of lower alkyl ($C_1C_4$), chloro, nitro, trifluoromethyl, or mono-substituted in the para-position by phenyl or benzyl (which may be unsubstituted or in turn substituted by one or two of such groups as mentioned above, especially at the para-position. A preferred $P^1$ is the diphenyl tertiary-butylsilyl radical.

$P^2$ is preferably unbranched alkyl having from 1 to 4 carbon atoms, especially methyl.

$P^3$ is preferably a bulky radical e.g. trityl, i.e. triphenylmethyl.

An alternative method of obtaining compounds VI is depicted in Reaction Scheme D, below, which can employ either compounds D or F as starting materials.

In Reaction Scheme D, $P^1$ and $P^2$ are as defined above. This alternative method is not part of the present invention, however.

REACTION SCHEME D

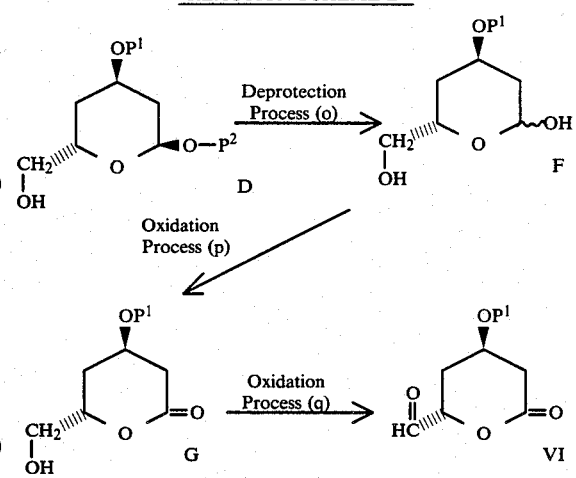

Compounds II may be converted to corresponding compounds III (process (i)) by reaction at the aldehyde position with a Wittig reagent of the formula VII:

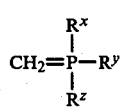

VII wherein each of $R^x$, $R^y$ and $R^z$ is, independently, an aryl radical. The reaction is conveniently carried out in an inert medium, e.g., a cyclic ether such as tetrahydrofuran at reduced temperatures, e.g. $-15°$ to $+5°$ C., such as $-10°$ to $0°$ C. under essentially anhydrous conditions when moisture-susceptible strong bases are employed. The reagent is prepared by treating a compound VIII:

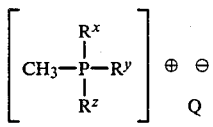   VIII in which $R^x$, $R^y$ and $R^z$ are as defined above, and Q is a higher halo (having an atomic weight of from about 34 to 120), e.g., chloro, bromo or iodo, with a strong base, such as an alkali metal salt of a hydrocarbon, e.g., n-butyl lithium, in an inert medium, such as cyclic ether, at reduced temperatures, e.g., from about −15° to 0° C., e.g., about −10° C. conveniently, the Wittig reagent is used in situ, so that the conditions and medium employed in its preparation are also utilized in its reaction.

In the Wittig reagent, lack of $R^z$, $R^x$ or $R^y$ is preferably phenyl which is unsubstituted or substituted by one or two lower alkyl ($C_1$–$C_4$) or chloro substituents. Preferably $R^x$, $R^y$ and $R_z$ are the same.

Compounds IV may be obtained by deprotecting corresponding compounds III at the 2-position thereof (process j). The deprotection may be accomplished by conventional means, e.g. by treatment with acidic conditions, e.g. using dilute acetic acid or hydrochloric acid e.g. at temperatures of from about 20° to 80° C., preferably in the presence of watermiscible cosolvent, such as tetrahydrofuran (THF).

A compound IV is converted to a corresponding compound V by oxidizing its 2-hydroxy function to a carbonyl function (process (k)). The oxidation may be accomplished in the conventional manner for converting a lactol to a lactone, e.g. by treatment with pyridinium chlorochromate, in an inert organic medium e.g. a halogenated hydrocarbon, such as methylene chloride, at moderate temperatures, e.g. at 20°–30° C.

Compounds V are converted to corresponding compounds VI by oxidation of the vinyl group to an aldehedic function (process (l)). The oxidation may be obtained by conventional means for oxidizing an olefinic position to a carbonyl function. A convenient method of carrying out process (l) is by treating a compound V in an inert medium e.g. a lower alkanol, such as methanol or a lower ester, such as ethyl acetate, with ozone at reduced temperatures, e.g. at from about −50° to −80° C. When the required amount of ozone has been reacted, the intermediate ozonide is decomposed by the addition of a mild reducing agent, such as dimethyl sulfide or triphenylphosphine to the reaction mixture to yield the desired aldehyde; a preferred method being use of ethylacetate and triphenylphosphine.

Final steps in the process are the reaction (process m) of the 4-protected hydroxy aldehyde II with a Wittig reagent bearing the desired Z-moiety (a compound X) to give a 4'-protected hydroxy form of a final product (E), which is then 4-deprotected (process n) to yield a desired final product (I).

In process (m), the Wittig reagent is prepared from a phosphonium reagent of the formula X:

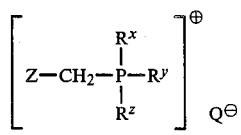   X wherein Z, $R^x$, $R^y$, $R^z$ and Q are as defined above. Reagents of formula X are obtainable in the conventional method for preparing such reagents; a convenient method is by reacting a compound of the formula X':

Z—CH$_2$—Q    X' in which Z and Q are as defined above, with a phosphine of the formula X":

    X"

in which $R^x$, $R^y$ and $R^z$ are as defined above, e.g. triphenyl phosphine, in an inert anhydrous organic solvent, for example a hydrocarbon such as benzene, toluene or xylene, or a mixture thereof, at a ratio of about 1-1.1 moles of phosphine (X") per mole of the halomethylindole (X'). The reaction temperature is conveniently 60° C. to reflux, preferably not in excess of 150° C., and, while the reaction time is inversely related to the reaction temperature, it is conveniently 2–8 hours. The reaction is run under essentially anhydrous conditions, e.g. in an inert atmosphere.

Compounds X' are obtainable by halogenating a corresponding alcohol of the formula X'":

Z—CH$_2$—OH    X'"

in which Z is as defined. The halogenation may be carried out in the conventional manner. Compounds X'", in turn are obtainable by reducing esters of formula $X^{IV}$:

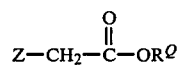    $X^{IV}$ in which Z is as defined above and $R^Q$ is methyl or ethyl preferably methyl. Compounds X are conveniently prepared by the method disclosed in Application Ser. No. 443,668 (filed Nov. 22, 1982) or its c.i.p. mentioned above.

The deprotection of a protected compound E to its corresponding compound I, may be accomplished in the conventional manner. Where the protecting group is a silyl-type, then acid treatment is employed, e.g., using a mixture of at least equal (e.g. 2 times) molar portions of acetic acid and tetrabutylammounium fluoride (TBAF) in THF, methanolic HCl, or fluoride anion reagents. Moderate temperatures may be employed, e.g., from about 20° to 60°, e.g., 20° to 30° C.

Reagents and starting materials described herein, e.g., compounds W, X" and $X^{IV}$ are known and obtainable by known means, or where not known, may be obtained by adaptation of methods reported in the literature for the preparation of known analogs; some compounds being commercially available.

With particular respect to the process steps of Reaction Scheme D, the deprotection of a compound D to a corresponding compound F (process (o)) may be accomplished in a similar manner to process (j), described above. Likewise, the oxidation of a compound G to a corresponding compound VI (process (q)) may be accomplished in the manner of process (h) described above.

The oxidation of a compound F to its corresponding compound G may be accomplished in the conventional manner of oxidizing a lactol to a lactone function. Preferably, a compound F is treated with bromine (neat) at moderate temperatures, e.g. 20° to 50° C., in the presence of aqueous sodium acetate. Preferably, a water miscible solvent is present, e.g. dimethyl formamide.

The final products and intermediate compounds described herein may be recovered and refined, where such is desired, by conventional means, such as by crystallization, distillation or chromatographic techniques such as column or thin layer chromatography, e.g., silica gel column chromatography.

Evaporations are done under vacuum employing minimal heating. Drying of organic phases is done over anhydrous sodium sulfate, unless indicated otherwise.

The following examples are illustrative of the invention. All temperatures are centigrade and room temperature is 20° to 30° C., unless indicated otherwise.

Where NMR characterization data is presented, the analysis is run in CDCl$_3$ and values given in ppm; digits in parenthesis are number of protons; and t=triplet, d=doublet, s=singlet, m=multiple and b is broad, and J is coupling factor, unless indicated otherwise.

EXAMPLE 1

(E)-trans-6-[1'-methyl-3'-(4''-fluorophenyl)indol-2'-ylethenyl]3,4,5,6-tetrahydro-4-hydroxy-2H-pyran-2-one (4R, 6S)

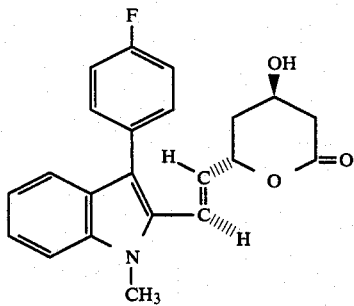

Step A, preparation of (acetato-o)(tetrahydro-4,5-dihydroxy-6-hydroxymethyl-2-methoxy-2H-pyran-3-yl)-mercury* (a compound X)

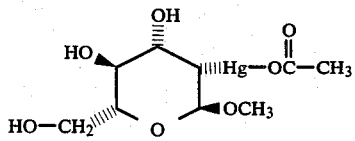

Under a nitrogen atmosphere, 300 m of metallic sodium is dissolved in one liter of methanol (freshly distilled from magnesium) over about 10 minutes, with stirring. 136.1 g of tri-O-acetyl-D-glucal** is added (as a solid), which dissolves, and the mixture is cooled and stirred at room temperature, for one hour at which time TLC indicates methanolysis is complete. 159.35 g of mercuric acetate is slurried in one liter of freshly distilled methanol. The slurry is added to the reaction mixture through an addition funnel having a widebore stopcock, portionwise, over a period of one hour. As each portion is added, it dissolves in a short time. After the addition is completed stirring is continued (at room temperature and under nitrogen gas) for an additional four hours, at which time the reaction mixture is homogeneous and colorless. Heat is gently applied by a bath (not over 40°) to remove (under vacuum) 1,200 ml of solvent. The residue begins to solidify as it cools; and scratching the inside of the vessel over a period of about 30 minutes results in a granular solid product. The solids are collected on a sintered-glass filter, and the vessel rinsed with 50 ml. of ice-cold dry methanol, which is used to wash the filtered solids. The solids are washed with 300 ml of dry diethyl ether, and then dried (under vaccum) to obtain the title product of this step as a fine white powder. If desired, a second crop may be obtained by adding enough methanol to the mother liquor to make it homogeneous, and then concentrating to a thick oil, which solidifies on standing, and on treatment as above, yields additional product as a white solid. The product of this step is either used promptly for the next step, or held under nitrogen if not used promptly.

*may also be called (4α,5β-dihydroxy 6α-hydroxymethyl-2β-methoxy-tetrahydro-2H-pyran-3-yl)mercuric acetate
**may also be called 3β,4α-dihydroxy-2α-hydroxymethyl-2,3-dihydro-2H-pyranyl triacetate Step B, preparation of 4α,5β-dihydroxy-6α-hydroxymethyl-2β-methoxy-tetrahydro-2H-pyran (a compound Y)

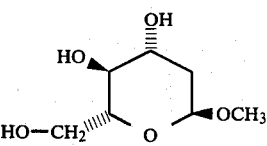

A slurry of 159.0 g of the product of Step A above and one liter of methanol (freshly distilled from magnesium) is prepared. To the slurry is added 33.5 g of finely powdered solid sodium chloride. The mixture is stirred for about 5 minutes at room temperature resulting in a homogeneous solution, except for excess sodium chloride. The mixture is then cooled to 0° C. (with an external ice bath) and 10.7 g of sodium borohydride which had been finely powdered, slurried in one liter of dry isopropanol freshly distilled from BaO) is placed in an addition funnel having a wide-bore stopcock (Agitation is necessary to maintain the mixture in suspension). The slurry is added in small portions over 1.5 hrs. with ice-bath cooling in order to maintain internal temperature below 25°, as the reaction is exothermic and produces a gas and metallic mercury). When the addition is completed, the ice-bath is removed, and the suspension (gray) is allowed to stir for two hours. Solvent is vacuum distilled off (at below 40°) until the residue is almost dry, and one liter of ethyl acetate (freshly distilled from P$_2$O$_5$) is added. The slurry is cooled to about 0° and concentrated hydrochloric acid then added dropwise, with vigorous stirring. (The pH is checked after each 5 drops of the acid addition) until slightly acid. 50 g of solid sodium bicarbonate is immediately added; the entire acidification should be completed in less than 5 minutes.

After stirring for about 5 minutes, 50 g of 4 A° molecular sieve is added, and the reaction mixture filtered through a pad of celite supported on glass-wool in a sintered glass funnel, pre-wetted with dry ethyl acetate. The gray sludge in the funnel is washed 3 times with 100 ml portions of dry ethyl acetate and the combined ethyl acetate extracts evaporated to a thick colorless gum. The gum is dried under high vacuum for 1 hr. then held for about 18 hrs. in a vacuum oven in the presence of P₂O₅, and then placed under high vacuum for one hour which results in a waxy solid which upon standing (5 hours) becomes less waxy. The solids are triturated with dry diethyl ether to give solid title product of this step, m.p. 64°–66° (softening at 63°).

Step C, preparation of 4α,5β-dihydroxy-2β-methoxy-6α-triphenylmethoxymethyl-tetrahydro-2H-pyran (a compound Z)

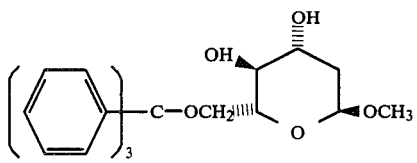

Under a nitrogen atmosphere 41.5 g of the triol product of Step B is mixed with one liter of pyridine (freshly distilled from potassium hydroxide) resulting in almost complete solution (as some solid remains in suspension, after ½ hr. stirring). 300 ml of dry dichloromethane is added with stirring, resulting in almost complete solution. 69.695 g of trityl chloride (solid) is added resulting in the solution turning slightly tan (without noticeable exotherm) and the mixture is stirred for about 18 hrs. under nitrogen during which a precipitate forms. The mixture is poured into 1.5 liters of ice-cold dilute hydrochloric acid (10%) and extracted 3 times with 200 ml portions of dichloromethane. The combined dichloromethane extracts are washed 6 times with 200 ml portions of ice-cold 10% hydrochloric acid, 2 times with 200 ml portions of saturated aqueous sodium bicarbonate, once with 200 ml of brine and then dried over anh. magnesium sulfate. The dried extracts are recovered by filtration and solvent removed under vacuum, to obtain a residue, which is a thick oil (partly solid, which smells of pyridine). The residue is redissolved in 500 ml of ethyl ether and 200 ml of dichloromethane, and the solution washed 5 times with 200 ml portions of ice-cold hydrochloric acid, twice with 200 ml portions of sat. aqueous sodium bicarbonate, once with brine, and dried over anhydrous magnesium sulfate. The dried solution (light yellow) is then evaporated under vacuum to obtain a tan foam, which is then dissolved in 200 ml of hot ethyl ether plus enough dichloromethane to make the mixture homogeneous. To the resulting solution is added pentane until cloudy, then allowed to stand at room temperature for about 48 hours, during which a precipitate forms. The solids are collected on a filter and washed with pentane to obtain the title product of this step, m.p. 140°–142°.

Step D, Preparation of 4β,5β-epoxy-2β-methoxy-6α-triphenylmethoxymethyl-tetrahydro-2H-pyran (a compound A)

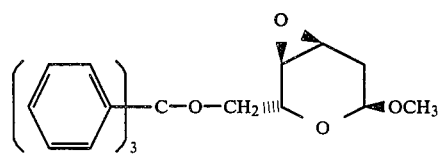

Under nitrogen, 9.6 g of sodium hydride (as a 50% dispersion in paraffin oil) is washed 3 times with 10 ml portions of pentane, 80 ml of hexamethylphosphoramide (HMPT) is added to the washed sodium hydride. 20.025 g of the diol product of Step C is dissolved in 100 ml of HMPT, the solution placed in an addition funnel and cautiously added therefrom to the mixture at room temperature over a period of about 15 minutes (gas evolves). The addition funnel is rinsed with 20 ml of HMPT and the rinse added to the mixture, which is then stirred for 1.5 hrs. at room temperature, (bubbling stops and the reaction mixture is a light tan color). The reaction mixture is diluted with 100 ml of dry THF (freshly distilled) and the mixture cooled to −30° under N₂. 16.72 g of 2,4,6-triisopropylbenzenesulfonyl imidazol in 100 ml of dry THF is added drop-wise to the mixture over a period of about 1 hr. (−30° temperature being maintained). After addition stirring is continued for 3 hrs. at −30°. The reaction mixture is filtered (through filter paper containing celite, pre-wetted with THF), and the solids washed on the filter with 100 ml of THF. The filtrate is concentrated by vacuum-evaporation to obtain a viscous oil, which is poured into 2.5 liters of brine and extracted 5 times with 150 ml portions of diethyl ether. The combined ether extracts are washed twice with 50 ml of brine, dried over anh. magnesium sulfate and evaporated to a residue (thick oil). 10 to 15 ml of dichloromethane is added to the residue which is then warmed, and pentane added to give a volume of about 300 ml. Upon standing for about 18 hours a precipitate forms which is washed with pentane and recovered as a white solid. The solid is recrystallized from pentane-diethylether to yield the title product of this step m.p. 100°–102°. Additional product can be recovered from the mother liquor, if desired. The product of this step is also known as 3,7-dioxabicyclo[4.1.0]heptane, 2-methoxy-4-triphenylmethoxy-2β,4α,6β,7β.

Step E, Preparation of 2β-methoxy-6α-triphenylmethoxymethyl-tetrahydro-2H-pyran-4β-ol (a compound B)

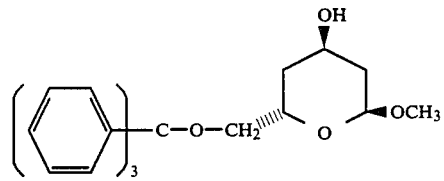

8.04 g. (20 mmole) of 4β,5β-epoxy 2β-methoxy-6α-triphenylmethoxymethyl-tetrahydro-2H-pyran is dissolved in 200 ml diethyl ether which is then cooled to 1° C. and 20 ml (20 mmole) of a 1 molar solution of lithium aluminum hydride in ether is added dropwise over five minutes maintaining the temperature at 1° C. After one hour at 1° C. and three hours at room temperature 20 ml of ethyl acetate is added slowly followed by 20 drops of H₂O. The reaction mixture is filtered through celitte and the solvent removed in vacuo to give 7.51 g. crude oil which crystallizes from ether-pentane to give 6.90 g. wt. solid. The solid is "flash chromatographed" on silica gel with 3% acetone in methylene chloride to give the title product of this step, with no trace of isomeric materials by TLC, in this fraction*. GC or C¹³ NMR. m.p. 101.5–103.5. [α]$_D^{25}$+47.14 (CHCl₃) [c=2.07]

*A small amount of the isomeric 2β-6α-triphenylmethoxymethyl-tetrahydro-2H-pyranol-5β-ol can then be recovered from the column.

Step F, Preparation of 2β-methoxy-4β-(diphenyl t-butylsiloxy)6α-triphenylmethoxy-methyl-tetrahydro-2H-pyran; a compound C

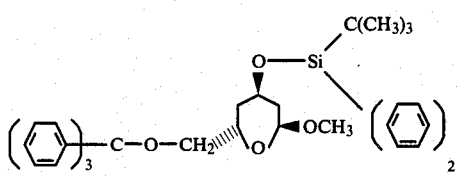

23.25 g (0.05 m) of the alcohol of Step E is dissolved in 207 ml of DMF*, 8.3 g of imidazole is added followed by 16.74 g of t-butyl diphenyl silyl chloride. When the reaction is complete, it is poured into 1 liter of brine and extracted 4 times with 200 ml portions ether. The ether phase is washed three times with 200 ml portions of cold 5% hydrochloric acid, 3 times with 200 ml portions of aqueous sat. sodium bicarbonate, dried over anh. sodium sulfate and evaporated in vacuo to a solid which is recrystallized from ether-hexane to obtain the product of this step as a white cryst. solid m.p. 151°–152° C.
*dimethylformamide

Step G, Preparation of 2β-methoxy-4β-(diphenyl t-butylsiloxy)6α-hydroxymethyl-tetrahydro-2H-pyran; a compound D

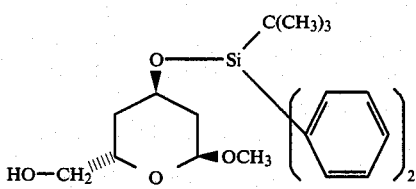

10 g (0.0156 moles) of trityl ether of Step F is dissolved in 300 ml of THF plus 30 ml of t-butyl alcohol. The solution is cooled to −40° C. and 300 ml of ammonia is condensed into the flask. Some cloudiness develops so an additional 170 ml of THF is added. The reaction is maintained at −40° C. while 2.3 g of sodium metal is added over 2 hours. When all the sodium has dissolved, a few chips of ice are added and the dark blue solution becomes colorless. The ammonia is allowed to boil off, the THF phase is filtered and then evaporated to a residue. The residue is taken up in ether, dried over anh. sodium sulfate and evaporated to obtain a residue. The residue is place on a short column of alumina (Activity III) which is eluted first with toluene to recover the by-product triphenylmethane and then with ethyl acetate to obtain the desired product of this step $[\alpha]_D^{25} = +63.56$ (CHCl₃, c=1.09)

Step H, Preparation of [4β-(diphenyl t-butylsiloxy)-6β-methoxy-tetrahydro-2H-pyran-2-yl]-aldehyde; a compound II

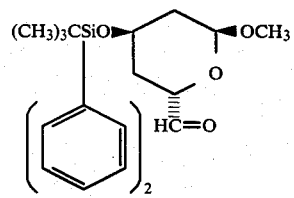

9.596 ml of oxalyl chloride dissolved in methylene chloride is cooled to −50° C. and a solution of 15.61 ml dimethyl sulfoxide (DMSO) dissolved in 50 ml methylene chloride is added at such a rate as to maintain −50° C. The mixture is stirred 2 minutes after addition is complete, followed by the addition of 4.006 g (0.01 moles) of the alcohol of Step F, dissolved in 10 ml methylene chloride over 5 minutes, maintained at −50° C. After 15 min. at −50° the mixture is treated with 69.69 ml of triethylamine in 50 ml methylene chloride and then stirred at −50° C. for 2 hours. Ten mls of brine is added and the cold reaction mixture is poured into 300 ml saturated aqueous sodium bicarbonate. The methylene chloride layer is separated, washed 3 times with aqueous sodium bicarbonate, 2 times with brine, dried over anhydrous sodium sulfate and concentrated to an oil which is chromatographed on silica gel with ether-hexane (1 to 9) to give a yellow oil, which shows carbonyl absorption at 1739 cm⁻¹ (IR); $[\alpha]_D^{25} + 51.66$ (CHCl₃, c=2.07).

Step I, 6α-vinyl-4β-(diphenyl t-butylsiloxy)-2β-methoxy-tetrahydro-2H-pyran (A compound III)

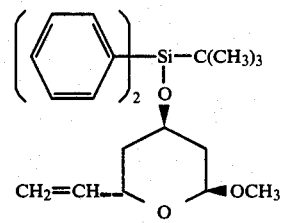

8.43 g (0.02 moles) of methyl triphenylphosphonium iodide is slurried in 150 ml of dry tetrahydrofuran under a nitrogen atmosphere and 12.9 ml of a 1.55 molar (0.02 moles) solution of butyl lithium in hexane is added dropwise over 10 minutes. The solution becomes homogenious with a light yellow color. After cooling to 0° C., 5.52 g (0.014 moles) of the aldehyde product of Step H (II), above, dissolved in 20 ml tetrahydrofuran is added over one half hour. The reaction mixture is allowed to come to room temperature and stirred for 18 hrs. Thin layer chromatography (silica gel-methylene chloride) indicates starting material is consumed. The reaction is poured into 200 ml brine and the tetrahydrofuran is removed in vacuo, the residue is extracted four times with 200 ml portions of diethyl ether, dried over anhydrous magnesium sulfate, filtered and concentrated to a brown syrup which is "flash chromatographed" on silica gel with 9:1 methylene chloridehexane to 3.20 g of a light yellow syrup $[\alpha_D] = +49.5$ (c=2.95, CHCl₃) 200 MHz NMR (CDCl₃) 7.65–7.75 (m,4H), 7.3–7.45 (m,6H), 5.7–5.9 (m,1H), 5.03–5.3 (m,2H), 4.7–4.8 (m,1H), 4.7 (t(J=3 Hz),1H), 4.12 (m,1H), 3.4 (S,3H), 1.5–1.8 (m,4H), 1.09 (S,9H).

Step J, 6α-vinyl-4β-(diphenyl t-butylsiloxy)-2α+2β-hydroxy-tetrahydro 2H-pyran (a compound IV)

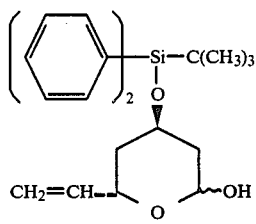

2.57 g (6.5 mmoles) of the olefinic product of step I, above, (III) is added to a mixture of 27.8 ml of glacial acetic acid, 18.5 ml of tetrahydrofuran and 18.5 ml of water and the solution heated to 70° C. When thin layer chromatography indicates starting material is gone (silica gel, 1:1 ether-hexane), i.e., about 2 hours, the solution is allowed to cool to room temperature, transferred to a one liter flask and brought to pH 7 by the addition of saturated sodium bicarbonate solution (gas evolution occurs). The neutral solution is concentrated in vacuo to remove tetrahydrofuran and the aqueous residue extracted twice with 200 ml portions of diethyl ether which are combined and then dried over anhyd. magnesium sulfate, filtered, and concentrated to 2.53 g of an oil which is a mixture of lactols (title products of this step) and is used as is for the following step (K).

Step K, 6α-vinyl-4β-(diphenyl t-butylsiloxy)-3,4,5,6-tetrahydro-2H-pyran-2-one (a compound V)

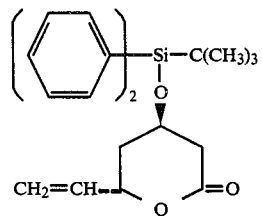

To 2.53 g (6.6 mmole) of the lactol product of step J, above, dissolved in 132 ml of methylene chloride at room temperature is added 4.26 g (20 mmoles) pyridinium chlorochromate as a solid. The reaction turns orange and then brown. After stirring for 18 hours, 350 ml of diethyl ether is added and the resulting precipitate removed via filtration through 50 g silica gel which is washed with 350 ml of diethyl ether. Concentration gives 2.41 g of a yellow oil which can be crystallized from cold hexane to give refined lactone product of this step as a white solid, m.p. 61°–62° C. IR ($CH_2Cl_2$) 1739 $cm^{-1}$ (C=O) $[\alpha]_D = +6.5$ ($CH_2Cl_2$, c=0.99)

200 MHz NMR ($CDCl_3$) 7.6–7.7 (m,4H), 7.35–7.5 (m,6H), 5.7–5.9 (m,1H), 5.15–5.35 (m,3H), 4.28 (m,1H), 2.4–2.7 (m,2H), 1.8–2.0 (m,1H), 1.55–1.7 (m,1H), 1.09 (S,9H).

Step L, [4β-(diphenyl t-butylsiloxy)-6-oxo-tetrahydro-2H-pyran-2-yl]aldehyde (a compound VI)

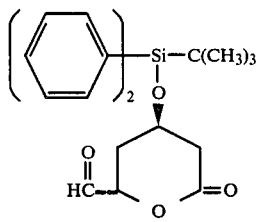

363.4 mg (0.956 mmole) of the lactone product of Step K (V) above, in 48 ml methanol cooled to −78° C., is treated with a stream of ozone introduced below the surface of the stirred solution, generated via a Welsbach Ozonator, for 3–4 minutes until a blue color is seen in the reaction mixture. Ozone treatment is stopped and 1 ml of dimethyl sulfide is added. The solution becomes colorless. The mixture is warmed to room temperature and the solvents removed in vacuo to yield a yellow oil, which can be chromatographed on silica gel with diethyl ether to give the desired aldehyde product of this step (usually as a mixture with its hydrate). NMR ($CDCl_3$) shows aldehyde proton at 9.76 ppm; IR ($CHCl_3$) 1742 $cm^{-1}$ (C=O); $[\alpha]_d = -6.9$ ($CHCl_3$, c=3.29).

When this step is carried out using equivalent amounts of ethyl acetate as reaction medium, and triphenylphosphine as reducing agent, a product of higher purity is more readily attained.

Step M, (E)-trans-6-[1′-methyl-3′-(4″-fluorophenyl) indol-2′-ylethenyl]3,4,5,6-tetrahydro-4-(diphenyl t-butylsilyl)-2H-pyran-2-one (4R,6S); (a compound E)

280.2 mg of [1-methyl-3-(4-fluorophenyl)indol-2-yl]methyl triphenyl phosphonium chloride is suspended in 10 ml of tetrahydrofuran at 0° C. and 337.6 μl of 1.55 molar butyl lithium in hexane is added. After 30 minutes of stirring, a homogenious red-orange solution results. A total of seven ml of this solution is added over 10 min. to 110.3 mg of the product of Step L dissolved in 5 ml THF at 0° C. The red-orange color is discharged immediately. Five ml. of saturated ammonium chloride solution is then added, followed by 20 ml of diethyl ether. The ether layer is washed with brine, dried over anhydrous magnesium sulfate, filtered and concentrated to a mixture of double bond isomers which is chromatographed on silica gel with methylene chloride to yield the title (E)-olefinic isomer.

Step N, (E)-trans-6-[1′-methyl-3′-(4″-fluorophenyl)indol-2′-ylethenyl]3,4,5,6-tetrahydro-4-hydroxy-2H-pyran-2-one (4R,6S); (a compound I)

50 mg of the olefinic product of Step M, above, is dissolved in 10 ml of dry THF, 5 equivalents of glacial acetic acid are added at room temperature followed by 3 equivalents of tetra-n-butyl ammonium fluoride (as a 1 molar solution in THF). The resulting mixture is stirred (at room temperature for about 18 hours. The mixture is then concentrated to a small volume and directly chromatographed on silica gel (eluted with 10% ethyl acetate in diethyl ether) to give the title product.

What is claimed is:

1. A compound of the formula:

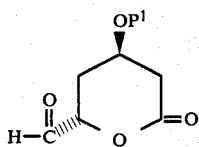

wherein $P^1$ is a tri-substituted silyl radical, the radicals being independently selected from the group consisting of (a) $C_4$ to $C_8$ tertiary alkyl, and (b) phenyl which may be unsubstituted or substituted by up to 2 $C_1$ to $C_4$ alkyl, chloro, nitro or trifluoromethyl substituents or mono- substituted in the para-position by phenyl or benzyl, which may be unsubstituted or substituted by one or two of said alkyl, chloro, nitro or trifluoromethyl substituents.

2. A compound of claim 1 in which tertiary alkyl is tertiary-butyl.

3. A compound of claim 1 which is [4β-(diphenyl t-butylsiloxy)-6-oxo-tetrahydro-2H-pyran-2-yl]aldehyde.

4. A compound of claim 1 in which any phenyl groups in $P^1$ are unsubstituted phenyl.

* * * * *